United States Patent
Ionkin et al.

(10) Patent No.: US 7,233,019 B2
(45) Date of Patent: Jun. 19, 2007

(54) ELECTROLUMINESCENT SILYLATED PYRENES, AND DEVICES MADE WITH SUCH COMPOUNDS

(75) Inventors: Alex Sergey Ionkin, Kennett Square, PA (US); Ying Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 459 days.

(21) Appl. No.: 10/831,845

(22) Filed: Apr. 26, 2004

(65) Prior Publication Data

US 2005/0238910 A1    Oct. 27, 2005

(51) Int. Cl.
*H01L 51/00* (2006.01)
*H01L 51/54* (2006.01)
*C09K 11/06* (2006.01)
*C07F 7/08* (2006.01)

(52) U.S. Cl. .................... 257/40; 313/504; 313/506; 428/690; 428/917; 136/263; 556/431; 556/432; 556/465; 556/489; 257/E51.046; 257/E51.049

(58) Field of Classification Search ............... None
See application file for complete search history.

(56) References Cited

U.S. PATENT DOCUMENTS

| | | | |
|---|---|---|---|
| 2005/0079385 A1* | 4/2005 | Nomura et al. | 428/690 |
| 2005/0095455 A1* | 5/2005 | Nomura et al. | 428/690 |
| 2005/0156164 A1* | 7/2005 | Sotoyama | 257/40 |

FOREIGN PATENT DOCUMENTS

| | | | |
|---|---|---|---|
| JP | 2001-332385 | * | 11/2001 |
| JP | 2002-63988 | * | 2/2002 |
| WO | WO 2004/096743 A1 | * | 11/2004 |

* cited by examiner

*Primary Examiner*—Marie Yamnitzky
(74) *Attorney, Agent, or Firm*—Barbara C. Siegell; Gail D. Tanzer

(57) ABSTRACT

This invention relates to electroluminescent silylated pyrene compounds. It also relates to electronic devices in which the active layer includes an electroluminescent silylated pyrene compound.

10 Claims, 1 Drawing Sheet

Figure 1 – Schematic of a light-emitting device
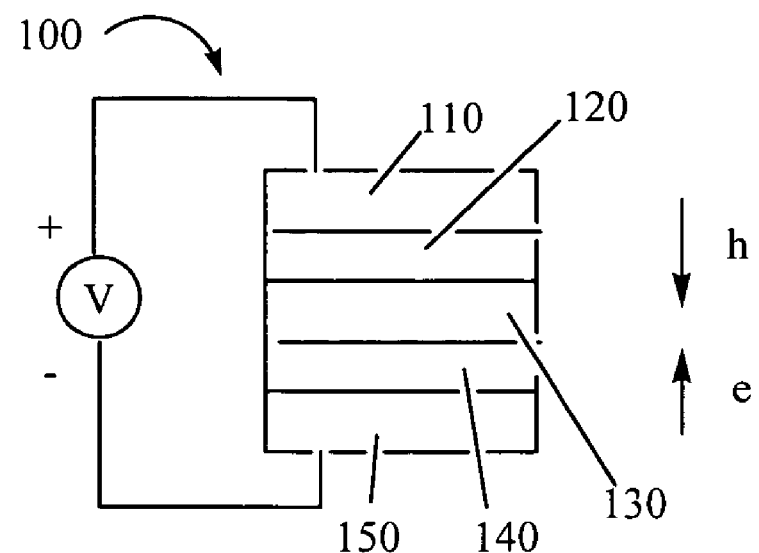

ELECTROLUMINESCENT SILYLATED PYRENES, AND DEVICES MADE WITH SUCH COMPOUNDS

BACKGROUND OF THE INVENTION

1. Field of the Invention

This invention relates to electroluminescent silylated pyrene compounds. It also relates to electronic devices in which the active layer includes an electroluminescent silylated pyrene compound.

2. Description of the Related Art

Organic electronic devices that emit light, such as light-emitting diodes (LEDs) that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence and some molecules of this type have been used to construct LEDs.

JP2002/63988 discloses light-emitting devices comprising fluorescent pyrenes, which may contain silyl groups, such as trimethylsilyl groups, or other bulky substituents.

However, there is a continuing need for electroluminescent compounds that are useful in devices such as LEDs.

SUMMARY OF THE INVENTION

The present invention is directed to a compound represented by Formula I:

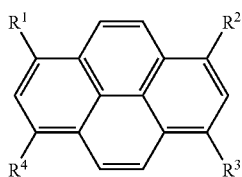

Formula I wherein:

$R^1$–$R^4$=H or an $Si(R^5)_3$-substituted aryl group;

$R^5$ is $C_1$–$C_6$ alkyl, $C_3$–$C_6$ cycloalkyl or $C_6$–$C_{10}$ aryl; and wherein at least one of $R^1$–$R^4$ is an $Si(R^5)_3$-substituted aryl group.

In another embodiment, the present invention is directed to an electronic device comprising at least one active layer between two electrical contact layers, wherein the at least one active layer comprises at least one compound represented by Formula I.

DESCRIPTION OF THE DRAWINGS

FIG. 1 is a schematic diagram of a light-emitting device (LED).

DETAILED DESCRIPTION OF THE PREFERRED EMBODIMENTS

The compounds of the invention are represented by Formula I:

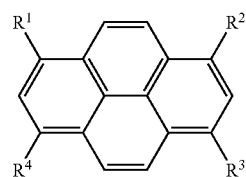

Formula I wherein:

$R^1$–$R^4$=H or an $Si(R^5)_3$-substituted aryl group; and $R^5$ is $C_1$–$C_6$ alkyl, $C_3$–$C_6$ cycloalkyl or $C_6$–$C_{10}$ aryl, wherein at least one of $R^1$–$R^4$ is an $Si(R^5)_3$-substituted aryl group.

Each of the substituents, $R^1$–$R^4$, can be selected independently, but for ease of synthesis it is preferred that $R^1=R^2=R^3=R^4$, i.e., that each $R^1$–$R^4$ be the same $Si(R^5)_3$-substituted group.

In addition to the silyl substituent, $Si(R^5)_3$, each of $R^1$–$R^4$ can be additionally substituted with alkyl or aryl groups. For example, each of $R^1$–$R^4$ can be a silyl-substituted tolyl group.

Each of $R^1$–$R^4$ can also contain more than one silyl group. For example, each of $R^1$–$R^4$ can be a bis(trimethylsilyl) phenyl group.

$R^5$ can also be silyl-substituted.

In one embodiment of Formula I, each of $R^1$–$R^4$ is a silyl-substituted aryl group, preferably a trialkylsilyl-substituted phenyl group. Most preferably, each of $R^1$–$R^4$ is trimethylsilylphenyl, where each of $R^1$–$R^4$ is

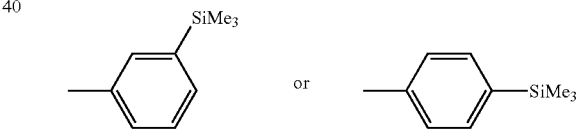

Silyl-substituted compounds represented by Formula I are readily synthesized via the so-called Suzuki coupling reaction. A Pd-catalyzed reaction of the appropriate mono-, di-, tri- or tetrachloro-substituted pyrenes with the appropriate silyl-substituted arylboronic acid gives the desired compounds represented by Formula I. In general, a slight excess of the boronic acid is used, relative to the number of chlorines on the pyrene. A base, e.g., cesium carbonate, is used to neutralize the HCl that is liberated in the coupling reaction. Tris(dibenzylideneacetone) dipalladium is a convenient catalyst to use, since its ligands are labile, but do not react with the other reagents under the reaction conditions. Other Pd catalysts can also be used. The phosphanes serve as stabilizing ligands for the Pd catalyst.

In one embodiment, the complexes having Formula I exhibit blue luminescence. In one embodiment, the complexes have photoluminescent and/or electroluminescent spectra that have a maximum at 500 nm or less.

The pyrene compounds represented by Formula I can be easily sublimed or volatilized. Thin films of these materials obtained via vacuum deposition exhibit good to excellent electroluminescent properties. It has been found that introduction of silyl-containing substituents onto the pyrene ring increases the volatility of the pyrenes and also makes them more readily soluble in organic solvents.

Examples of silyl-substituted pyrene compounds include, but are not limited to, Formulas II and III, shown below.

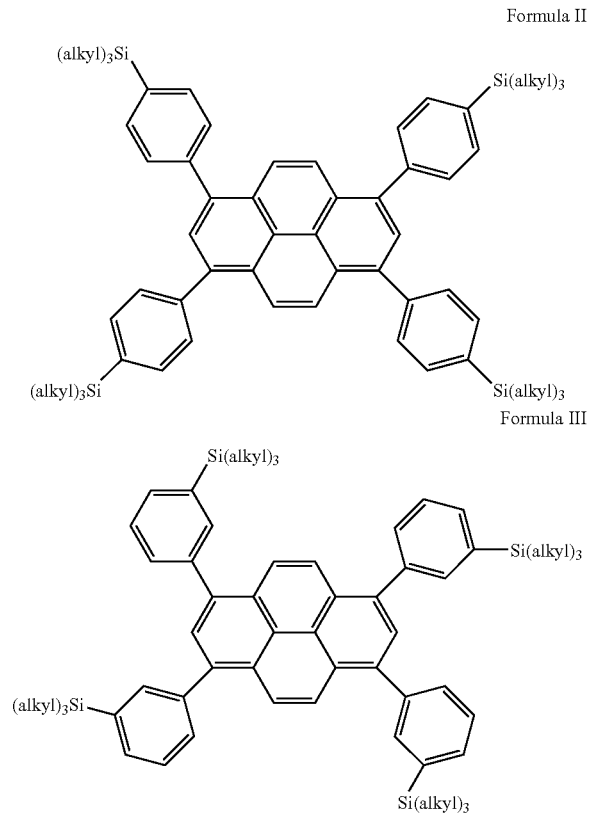

The alkyl groups of Formulas II–III can be $C_1$–$C_6$ alkyl or $C_3$–$C_6$ cycloalkyl groups.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. The term "alkaryl" refers to an alkyl-substituted aryl group. The term "aralkyl" refers to an aryl-substituted alkyl group.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Electronic Device

The present invention also relates to an electronic device comprising at least one photoactive layer positioned between two electrical contact layers, wherein the at least one photoactive layer of the device includes the silyl-substituted compound of the invention. Devices frequently have additional hole transport and electron transport layers. A typical structure is shown in FIG. 1. The device 100 has an anode layer 110 and a cathode layer 150. Adjacent to the anode is a layer 120 comprising hole transport material. Adjacent to the cathode is a layer 140 comprising an electron transport material. Between the hole transport layer and the electron transport layer is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photo-conductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The silyl-substituted compounds of the invention are particularly useful as the photoactive material in layer 130, or as electron transport material in layer 140. Preferably the silyl-substituted compounds of the invention are used as the light-emitting material in diodes. Additional materials can be present in the emitting layer with the silyl-substituted pyrene compound. For example, a fluorescent dye may be present to alter the color of emission. A diluent may also be added and such diluent may be a charge transport material or an inert matrix. A diluent may comprise polymeric materials, small molecule or mixtures thereof. A diluent may act as a processing aid, may improve the physical or electrical properties of films containing the silyl-substituted pyrene compound, may decrease self-quenching in the pyrene compounds described herein, and/or may decrease the aggregation of the pyrene compounds described herein. Non-limiting examples of suitable polymeric materials include poly(N-vinyl carbazole) and polysilane. Non-limiting examples of suitable small molecules includes 4,4'-N, N'-dicarbazole biphenyl or tertiary aromatic amines. When a diluent is used, the silyl-substituted pyrene compound is generally present in a small amount. In one embodiment, the pyrene compound is less than 20% by weight, based on the total weight of the layer. In one embodiment, the pyrene compound is less than 10% by weight, based on the total weight of the layer.

To achieve a high efficiency LED, the HOMO (highest occupied molecular orbital) of the hole transport material should align with the work function of the anode, the LUMO (lowest un-occupied molecular orbital) of the electron transport material should align with the work function of the cathode. Chemical compatibility and sublimation temperature of the materials are also important considerations in selecting the electron and hole transport materials.

The other layers in the OLED can be made of any materials that are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Group 8–10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1–18 (CRC Handbook of Chemistry and Physics, $81^{st}$ Edition, 2000). The anode 110 may also comprise an organic material such as polyaniline as described in "Flexible light-emitting diodes made from soluble conducting polymer," Nature vol. 357, pp 477–479 (11 Jun. 1992). At least one of the anode and cathode should be at least partially transparent to allow the generated light to be observed. Examples of hole transport materials for layer 120 have been summarized for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), small molecule: 4,4'-bis[N-(1-naphthyl)-N-phenylamino]biphenyl (NPB or NPD), carbazole biphenyl (CBP), polymeric: polypyrroles, polythiophenes, such as poly(3,4-ethylenedioxythiophene) (PEDOT), and porphyrinic compounds, such as copper phthalocyanine. Selected commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate.

Examples of electron transport materials for layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500–5000 Å, preferably 1000–2000 Å; hole transport layer 120, 50–1000 Å, preferably 200–800 Å; light-emitting layer 130, 10–1000 Å, preferably 100–800 Å; electron transport layer 140, 50–1000 Å, preferably 200–800 Å; cathode 150, 200–10000 Å, preferably 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the silyl-substituted pyrene compounds of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable.

Additional layers can also be added to tailor the energy levels of the various layers and facilitate electroluminescence.

The silyl-substituted pyrene compounds of the invention often are photoluminescent and may be useful in applications other than OLEDs.

EXAMPLES

The following examples illustrate certain features and advantages of the present invention. They are intended to be illustrative of the invention, but not limiting. All percentages are by weight, unless otherwise indicated.

4-Trimethylsilylphenylboronic acid, 3-trimethylsilylphenylboronic acid, tris(dibenzylideneacetone)dipalladium, and 1,3,6,8-tetra-chloropyrene were purchased from Sigma-Aldrich Co., Milwaukee, Wis.

Preparation of Di-tert-butyl-trimethylsilylmethyl-phosphane $^tBu_2P—CH_2—SiMe_3$ 50.00 g (0.277 mol) of di-t-butylchlorophosphine, 304 ml of 1.0 M pentane solution of (trimethylsilylmethyl)lithium and 150 ml of THF) were refluxed under argon for 3 days. The reaction mixture was allowed to cool to RT and an aqueous solution of ammonium chloride was added slowly. The organic phase was separated, and dried with magnesium sulfate. After removal of the solvent, the product was purified by distillation under vacuum. The yield of di-tert-butyl-trimethylsilylmethyl-phosphane was 55.32 g (86%) with b.p. 50–52° C./0.5 mm. 31-P-NMR (C6D6)+20.05 ppm. 1H NMR (C6D6) 0.01 (s, 9H, SiMe3), 0.23 (d, 2H, 2JPH=5.34 Hz, P—CH2-SiMe3), 0.91 (s, 9H, Me3C), 0.93 (s, 9H, Me3C). Elemental analysis: C, 61.89; H, 12.53; P, 13.25.

This material was used without further purification in the examples below.

Example 1

1,3,6,8-Tetrakis-(4-trimethylsilyl-phenyl)-pyrene

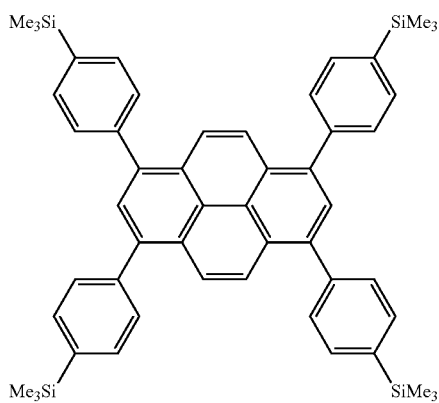

1,3,6,8-Tetrachloro-pyrene (3.50 g, 0.0103 mol), 4-trimethylsilylphenylboronic acid (10.0 g, 0.0515 mol), tris(dibenzylideneacetone)dipalladium(0) (1.18 g, 0.00129 mol), di-tert-butyl-trimethylsilylmethyl-phosphane (0.72 g, 0.0031 mol), cesium carbonate (16.78 g, 0.0515 mol) and dioxane (100 ml) were stirred at room temperature for 24 hours. The resultant mixture was poured into 200 ml of water and extracted twice with 200 ml of methylene chloride. The organic phase was dried over magnesium sulfate overnight and filtered. The solvent was removed on a roto-evaporator and the residue was purified by chromatography on silica gel with petroleum ether/ethyl ether (10/0.5) as eluent. Yield of 1,3,6,8-tetrakis-(4-trimethylsilanyl-phenyl)-pyrene was 2.39 g (29.11%) as a yellow solid with no m.p. below 250° C. $^1$H NMR (CD$_2$Cl$_2$) 0.15 (s., 36H, Me), 7.40–7.60 (br., 22H, arom-H), 7.91 (s., 2H, arom.-H), 8.20 (s., 4H, arom.-H). LC/MS: exact mass calculated for $C_{52}H_{58}Si_4$: 794.36. Found: 794.36. The structure was confirmed by X-ray analysis.

The emission spectrum of 1,3,6,8-tetrakis-(4-trimethylsilanyl-phenyl)-pyrene shows a maximum at 435 nm in dichloromethane.

Example 2

1,3,6,8-Tetrakis-(3-trimethylsilyl-phenyl)-pyrene

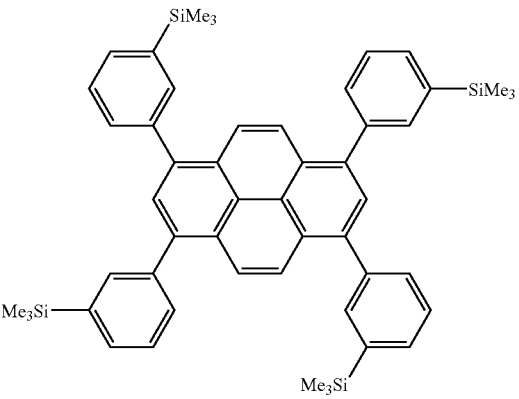

1,3,6,8-Tetrachloro-pyrene (4.38 g, 0.0129 mol), 3-trimethylsilylphenylboronic acid (15.0 g, 0.0773 mol), tris(dibenzylideneacetone)dipalladium(0) (1.77 g, 0.00193 mol), di-tert-butyl-trimethylsilylmethyl-phosphane (1.08 g, 0.0047 mol), cesium carbonate (25.17 g, 0.0773 mol) and dioxane (100 ml) were stirred at room temperature for 24 hours. The resultant mixture was poured into 200 ml of water and extracted twice with 200 ml of methylene chloride. The organic phase was dried over magnesium sulfate overnight and filtered. The solvent was removed on a roto-evaporator and the residue was purified by chromatography on silica gel using petroleum ether/ethyl ether (10/0.5) as eluent. Yield of 1,3,6,8-tetrakis-(3-trimethylsilyl-phenyl)-pyrene was 1.30 g (12.68%) as a yellow solid with no m.p. below 250° C. $^1$H NMR (CD$_2$Cl$_2$) 0.20 (s., 36H, Me), 7.40–8.20 (br., 28H, arom-H). LC/MS: exact mass calculated for $C_{52}H_{58}Si_4$: 794.36. Found: 794.36.

The emission spectrum of 1,3,6,8-tetrakis-(3-trimethylsilyl-phenyl)-pyrene shows a maximum at 420 nm in dichloromethane.

Example 3

OLED devices were fabricated by the thermal evaporation technique. The base vacuum for all of the thin film deposition was in the range of $10^{-6}$ torr. The deposition chamber was capable of depositing eight different films without the need to break up the vacuum. Patterned indium tin oxide (ITO) coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor. The cleaned, patterned ITO substrate was then loaded into the vacuum chamber and the chamber was pumped down to $10^{-6}$ torr. The substrate was then further cleaned using an oxygen plasma for about 5 minutes. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor. The completed OLED device was then taken out of the vacuum chamber and characterized immediately without encapsulation.

The OLED samples were characterized by measuring their (1) current-voltage (I–V) curves, (2) electroluminescence radiance versus voltage, and (3) electroluminescence spectra versus voltage. The I–V curves were measured with a Keithley Source-Measurement Unit Model 237. The electroluminescence radiance (in the unit of $cd/m^2$) vs. voltage was measured with a Minolta LS-110 luminescence meter, while the voltage was scanned using the Keithley SMU. The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table I summarizes device configuration and efficiency of OLED devices fabricated using materials disclosed in the present invention. MPMP is the hole transport material, DPA is the electron transport material, AlQ is the electron injection material, and DNA-anthracene is the host material. Their molecular structures are shown in the following:

TABLE I

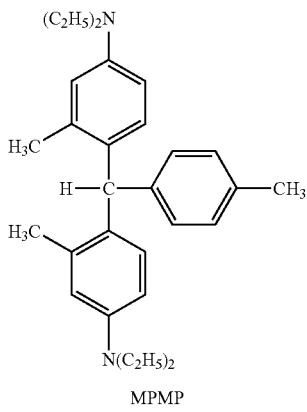

MPMP

TABLE I-continued

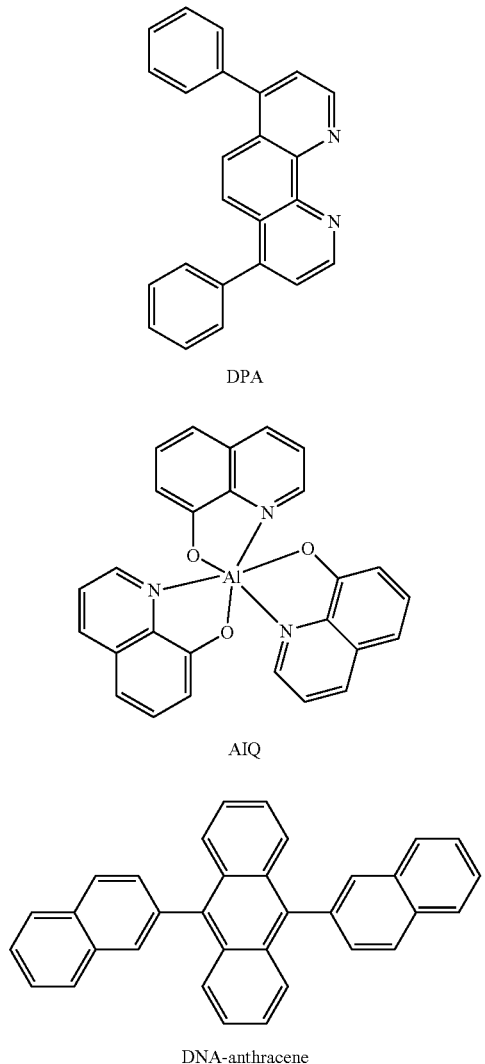

DPA

AlQ

DNA-anthracene

Device configurations and efficiency of OLED device

| Emitter | Hole transport material | Electron transport material | Peak Efficiency, cd/A | Peak Radiance cd/m2 | Peak wavelength, nm |
|---|---|---|---|---|---|
| Example 2 in DNA-anthracene, 13 wt % | MPMP | DPA | 0.6 | 700 cd/m2 | 450 + 490 nm |

Device configuration: MPMP(302Å)/13 wt % Exp 2 in DNA-anthracene (220Å)/DPA(102Å)/AlQ(305Å)/LiF(10Å)/Al(505Å)

What is claimed is:

1. An organic electronic device comprising at least one active layer between two electrical contact layers, wherein the at least one active layer comprises a compound represented by Formula I

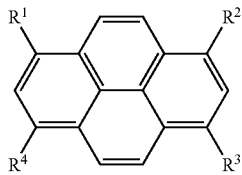

Formula I wherein:
R$^1$–R$^4$=H or an Si(R$^5$)$_3$-substituted aryl group, wherein said Si(R$^5$)$_3$-substituted aryl group is a substituted aryl group having at least one Si(R$^5$)$_3$ group as a substituent, provided any substituents other than Si(R$_5$)$_3$ groups are alkyl or aryl groups;
R$^5$ is C$_1$–C$_6$ alkyl or silyl-substituted C$_1$–C$_6$ alkyl, C$_3$–C$_6$ cycloalkyl or silyl-substituted C$_3$–C$_6$ cycloalkyl, or C$_6$–C$_{10}$ aryl or silyl-substituted C$_6$–C$_{10}$ aryl; and wherein at least one of R$^1$–R$^4$ is an Si(R$^5$)$_3$-substituted aryl group.

2. The organic electronic device of claim 1, wherein the active layer is a light-emitting layer.

3. The organic electronic device of claim 1, wherein the active layer is a charge transport layer.

4. The device of claim 1, wherein each of R$^1$–R$^4$ is an Si(R$^5$)$_3$-substituted aryl group, and R$^1$=R$^2$=R$^3$=R$^4$.

5. The device of claim 4, wherein the Si(R$^5$)$_3$-substituted aryl group is a trimethylsilylphenyl group.

6. The device of claim 1, wherein the at least one active layer further comprises a diluent selected from the group consisting of poly(N-vinyl carbazole), polysilane, 4,4'-N,N'-dicarbazole biphenyl, and tertiary amines.

7. The device of claim 1, further comprising a hole transport layer comprising a hole transport material selected from the group consisting of: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylpheny)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4'-bis[N-(1-naphthyl)-N-phenylamino]biphenyl (NPB or NPD), carbazole biphenyl (CBP), polymeric polypyrroles and polythiophenes, porphyrinic compounds, and combinations thereof.

8. The device of claim 1, further comprising an electron transport layer comprising an electron transport material selected from the group consisting of tris(8-hydroxyquinolato)aluminum (Alq3); 2,9-dimethyl-4,7-diphenyl-1,10-phenanthroline (DDPA); 4,7-diphenyl-1,10-phenanthroline (DPA); 2-(4-biphenylyl)-5-(4-t-butylphenyl)-1,3,4-oxadiazole (PBD); 3-(4-biphenylyl)-4-phenyl-5-(4-t-butylphenyl)-1,2,4-triazole (TAZ) and combinations thereof.

9. A compound represented by Formula I

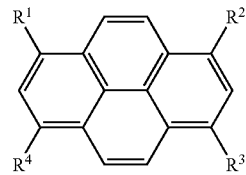

Formula I wherein:
R$^1$–R$^4$=H or an Si(R$^5$)$_3$-substituted aryl group, wherein said Si(R$^5$)$_3$-substituted aryl group is a substituted aryl group having at least one Si(R$^5$)$_3$ group as a substituent, provided any substituents other than Si(R$_5$)$_3$ groups are alkyl or aryl groups;
R$^5$ is C$_1$–C$_6$ alkyl or silyl-substituted C$_1$–C$_6$ alkyl, C$_3$–C$_6$ cycloalkyl or silyl-substituted C$_3$–C$_6$ cycloalkyl, or C$_6$–C$_{10}$ aryl or silyl-substituted C$_6$–C$_{10}$ aryl; and wherein at least one of R$^1$–R$^4$ is an Si(R$^5$)$_3$-substituted aryl group.

10. The compound of claim 9, wherein R$^1$=R$^2$=R$^3$=R$^4$=Si(R$^5$)$_3$-substituted aryl group; R$^5$ is selected from the group of C$_1$–C$_6$ alkyl and C$_3$–C$_6$ cycloalkyl groups, and the compound is represented by Formula II or Formula III:

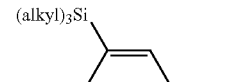

Formula II

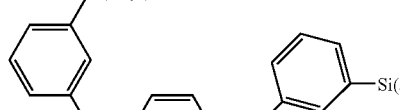

Formula III

* * * * *